United States Patent
Lyons et al.

(10) Patent No.: US 8,911,495 B2
(45) Date of Patent: Dec. 16, 2014

(54) RELIABLY RETAINED SHAPE MEMORY OPHTHALMOLOGICAL IMPLANTS

(75) Inventors: Michael B. Lyons, Boulder, CO (US); Julie Marie Trommeter, Lafayette, CO (US); Naresh Mandava, Denver, CO (US); Malik Kahook, Denver, CO (US); Robin Shandas, Boulder, CO (US); James Fogelberg, Boulder, CO (US); Jeffrey Paul Castleberry, Longmont, CO (US)

(73) Assignees: Endoshape, Inc., Boulder, CO (US); The Regents of The University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/257,196

(22) PCT Filed: Mar. 16, 2010

(86) PCT No.: PCT/US2010/027526
§ 371 (c)(1),
(2), (4) Date: Dec. 23, 2011

(87) PCT Pub. No.: WO2010/107826
PCT Pub. Date: Sep. 23, 2010

(65) Prior Publication Data
US 2012/0116504 A1    May 10, 2012

(51) Int. Cl.
| | |
|---|---|
| *A61F 2/14* | (2006.01) |
| *A61F 9/007* | (2006.01) |
| *A61M 31/00* | (2006.01) |
| *A61L 27/50* | (2006.01) |
| *A61L 27/14* | (2006.01) |
| *A61L 27/04* | (2006.01) |
| *A61M 25/01* | (2006.01) |
| *A61M 25/04* | (2006.01) |
| *A61M 25/00* | (2006.01) |
| *A61F 9/00* | (2006.01) |

(52) U.S. Cl.
CPC .......... *A61F 9/00772* (2013.01); *A61M 25/01* (2013.01); *A61M 25/04* (2013.01); *A61M 25/00* (2013.01); *A61M 31/002* (2013.01); *A61F 2210/0014* (2013.01); *A61L 2400/16* (2013.01); *A61L 27/50* (2013.01); *A61L 2430/16* (2013.01); *A61L 27/14* (2013.01); *A61F 9/0017* (2013.01); *A61L 27/04* (2013.01)
USPC ............................................... 623/4.1; 604/8

(58) Field of Classification Search
USPC .................................................. 604/8; 623/4.1
See application file for complete search history.

(56) References Cited

U.S. PATENT DOCUMENTS 6,082,362 A * 7/2000 Webb ............................ 128/846
6,719,750 B2    4/2004 Varner et al.
(Continued)

FOREIGN PATENT DOCUMENTS

WO    2009/032328 A1    3/2009

OTHER PUBLICATIONS

PCT International Search Report dated Dec. 6, 2010, PCT Application No. PCT/US2010/027526, 2 pages.
(Continued)

*Primary Examiner* — David H Willse
*Assistant Examiner* — Tiffany Shipmon
(74) *Attorney, Agent, or Firm* — Dorsey & Whitney LLP

(57) ABSTRACT

An implantable ophthalmological device (10) in the form of a punctal plug or canalicular implant is configured for use at or near the nasolacrimal drainage system. In a deployed state, the device (10) may include an elongated body (25), an anchor (15) operably connected to the elongated body (25), a radially expanding occlusive feature disposed on an outer circumference of the elongated body (32), and a flange (30). The elongated body (25) may define a lumen (35) configured to receive a pharmacological treatment (55). The device (10) is made of a shape memory material such as a shape memory polymer.

16 Claims, 10 Drawing Sheets

(56) References Cited

U.S. PATENT DOCUMENTS

2004/0254516 A1  12/2004  Murray et al.
2007/0233037 A1* 10/2007  Gifford, et al. ............... 604/521
2007/0243230 A1* 10/2007  de Juan et al. ............... 424/427
2007/0298075 A1* 12/2007  Borgia et al. ............... 424/428
2011/0196487 A1*  8/2011  Badawi et al. ............... 623/4.1

OTHER PUBLICATIONS

Supplementary European Search Report dated Aug. 28, 2012, European Application No. 10 75 3999, 3 pages.

* cited by examiner

RELIABLY RETAINED SHAPE MEMORY OPHTHALMOLOGICAL IMPLANTS

CROSS REFERENCE TO RELATED APPLICATIONS

This application claims the benefit of priority pursuant to 35 U.S.C. §119(e) of U.S. provisional application No. 61/160,612 filed 16 Mar. 2009 entitled "Reliably retained shape memory polymer punctal plugs," which is hereby incorporated herein by reference in its entirety for the purposes of PCT Rule 20.6.

FIELD OF TECHNOLOGY

The technology disclosed herein relates to ophthalmological devices and methods of using such devices. More specifically, the technology relates to implants for use in or near the nasolacrimal drainage system, adjacent to the eye, embodying canalicular implants, commonly called punctal plugs for treatment of dry eye and time release of topical pharmacological treatments for the eye.

BACKGROUND

Ophthalmology is the branch of medicine which deals with the diseases and surgery of the visual pathways, including the eye, brain, and areas surrounding the eye, such as the lacrimal system and eyelids. The lacrimal apparatus or system is the physiologic system containing the orbital structures for tear production and drainage. It consists of the lacrimal gland, which secretes the tears, and its excretory ducts, which convey the fluid to the surface of the eye and the lacrimal canaliculi, the lacrimal sac, and the nasolacrimal duct, by which the fluid is conveyed into the cavity of the nose.

For certain types of treatment, it may be desirable to implant a medical device, such as a punctal plug, in the patient's ocular punctum, the drainage orifice near the eye, which provides a flow path for tear fluid from the eye to the canalicular lumen. For example, in order to treat dry eye, a punctal plug may be used to block the tear drainage by closing the lumen of the ocular punctum as treatment for the condition. These simple devices provide only the benefit of closing the lumen.

Often topical pharmacological treatments are prescribed in the form of liquid eye drops However, pharmacological treatments may be difficult for the patient to apply or patients may have difficulty in maintaining an accurate time regime for re-applying the drug and maintaining levels. For example, in treating glaucoma, which is typically condition of the elderly, patients may have difficulty with standard therapies that require application of liquid drops.

More recently, researchers and medical companies have identified the probable benefit from inducing an eluting drug into the device such that in contact with the tear fluid, the eluting drug provides a continual dosage of a drug for achieving and maintaining appropriate therapeutic levels. However, typical punctal plugs, once placed, may migrate internally, such as into the canalicular lumen, or externally, such as when it is released or expelled from the punctum. The migration may be caused by patient discomfort, such as by rubbing the eye or by blinking, squinting, blowing the nose, or sneezing.

The information included in this Background section of the specification, including any references cited herein and any description or discussion thereof, is included for technical reference purposes only and is not to be regarded subject matter by which the scope of the invention is to be bound.

SUMMARY

With the inherent advantages of shape memory polymer (SMP) materials, wherein tailored mechanical properties and temperature induced shape change, can allow an implantable SMP ophthalmological device to be easily/simply inserted, deploy significant features for reliable retention after insertion, and maintain a flexibility/softness to ensure patient comfort both internally and externally. In one implementation, an SMP punctal plug can enter the narrow ocular punctum opening and expand with features both above and below the ostium to provide good mechanical capture and retention.

The implementation of SMP materials in an ophthalmological implant device provides the ability to deploy much larger and more complex features, than known devices or designs, to enhance device retention in-situ. The mechanical properties of SMP materials can be tailored to achieve the preferred stiffness or softness for each aspect of insertion or wear. The "shape fixity" of SMP materials (i.e., representing two definitive and accurate shapes, those of pre- and post-thermal deployment) provides the ability to accurately define and provide an insertion configuration and separately define and provide a deployment configuration. Further, the nature of these features can be designed to provide for differential action to allow for ease of insertion, removal, and enhanced patient comfort during deployment-wear.

Achieving consistent therapeutic levels of drug in the eye is dependent upon two primary factors: a) the elution function of the drug in formulation (e.g., a lyophilized powder/tablet, or a matrix of drug/polymer that dissolves, etc); and b) the reliability of maintaining the device in the ocular punctum. Demonstrating overall clinical efficacy of this therapy requires that the plugs be reliably retained in the ocular punctum between physician office visits and for the prescribed duration of the eluting drug. Once that period is achieved, the drug may be replaced (as in a cartridge) or the device may be removed and replaced to impart new eluting drug and continuation of therapy, as needed. The resident drug eluting device does not require patient intervention and may improve patient compliance with the drug therapy.

An implantable ophthalmological device is disclosed herein that may be implanted in a patient's ocular punctum with increased safety, increased retention after insertion, increased patient comfort, and that may be used to deliver pharmacological treatments. In one embodiment, the device includes an elongated body having a proximal end and a distal end, an anchor operably connected to the distal end of the elongated body, a radially expanding occlusive feature disposed on an outer circumference of the elongated body, and a flange operably connected to the proximal end of the elongated body. In some embodiments, the elongated body defines a lumen or cavity. In some embodiments, the lumen or cavity may be configured to receive a pharmaceutical preparation. In some embodiments, the lumen or cavity may be configured to receive a key member. In some embodiments, the device is made of a shape memory polymer. In some embodiments, the device is made of a shape memory alloy.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION

Figure 1:
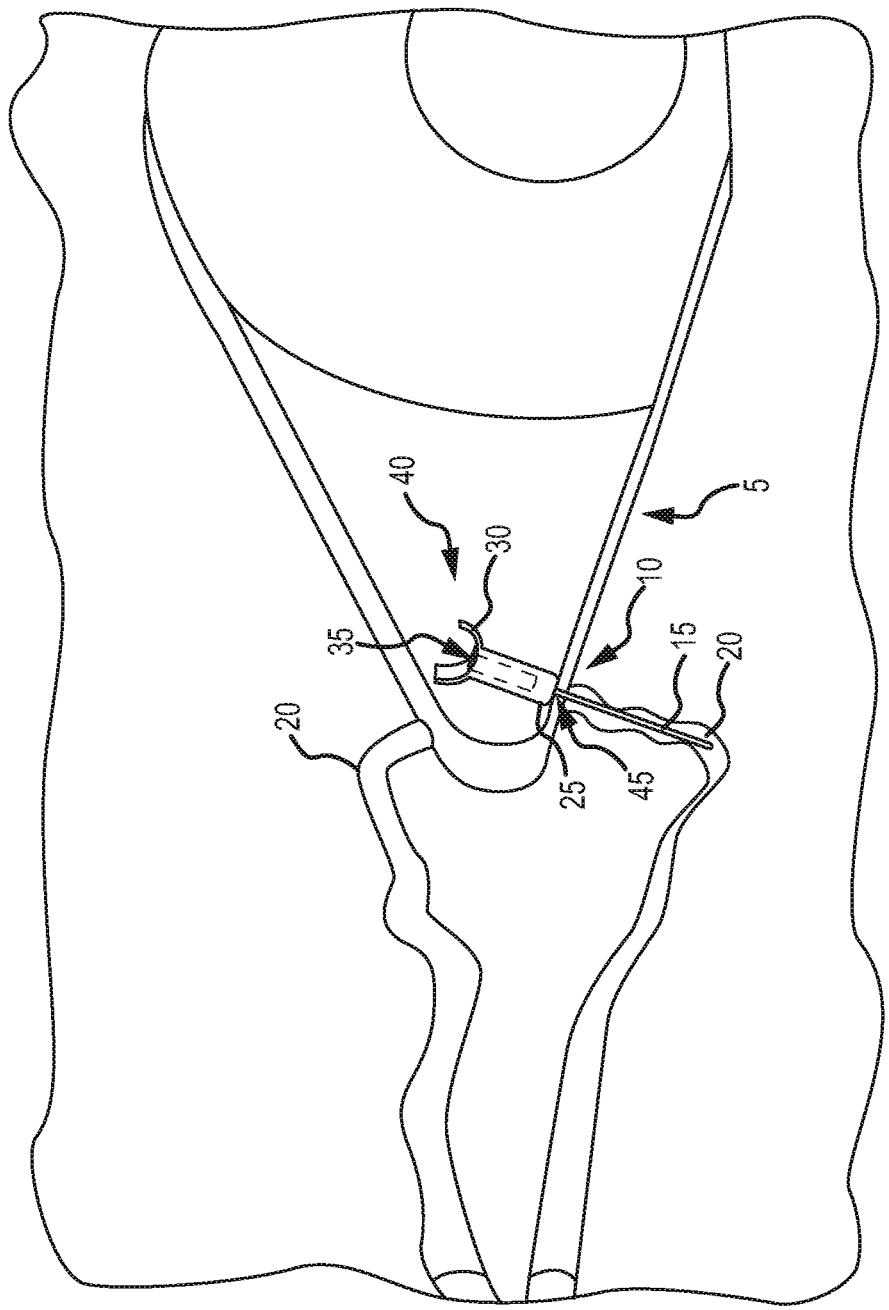
FIG. 1 is a partially transparent, schematic view of an implementation of an implantable ophthalmological device including an anchor wherein the device is shown in a non-deployed state as it is implanted in an ocular punctum of a human eye.

The present disclosure describes an implantable ophthalmological device, such as a punctal plug or canalicular implant, configured for use at or near the nasolacrimal drainage system. In some embodiments, the device may include an elongated body, an anchor operably connected to the elongated body, a radially expanding occlusive feature disposed on an outer circumference of the elongated body and a flange. In some embodiments, the elongated body defines a lumen or cavity configured to receive a pharmaceutical treatment. In some embodiments, the device is made of a shape memory polymer (SMP).

The ophthalmological device disclosed herein may be formed as a punctal plug to improve the reliability of retaining the occlusive device in the ocular punctum, e.g., over extended drug delivery times. In some implementations, the drug delivery time may be for up to 3 months. Achieving consistent therapeutic levels of drug in the eye may be dependent upon at least two factors: a) the elution function of the drug in formulation (e.g., a lyophilized powder/tablet or a matrix of drug/polymer that dissolves); and b) the reliability of maintaining the device in the ocular punctum. The device may be reliably retained in the ocular punctum between clinician office visits and for the prescribed duration of the eluting drug. Once that period is achieved, either the drug may be replaced (as in a cartridge) or the device may be removed and replaced to impart new eluting drug and continuation of therapy, as needed. Further, the steps to insert and release the device in place are relatively simple, thus the device reduces the time required for insertion.

Known prior art devices made from elastomeric materials may suffer from compromises made in providing a device stiff enough to handle/insert into the small ocular punctum and yet soft enough to assure patient comfort. If the material is too stiff, it can affect patient comfort. If the material is too soft, it can be difficult to insert or the retention features are ineffective.

In contrast to prior devices, the "shape fixity" of a punctal plug device using SMP materials (representing two definitive and accurate shapes, those of pre- and post-thermal deployment and described herein as the non-deployed state and the deployed state, respectively) provides the ability to accurately define and provide an insertion configuration (the non-deployed state) and separately define and provide a deployment configuration (deployed state). These definitive shapes and features may enhance the effectiveness of the SMP retention features over other shape change methods (e.g., other shape memory "crystalline polymeric material" that melts into a non-specific gel plug). Shape fixity also provides advantages over other devices made of elastomeric material or even metal that are subject to the limitations associated with deflecting or compressing features in that material's elastic regime. Other device retention features including barbs, coils, collarettes, and others are limited in size due to this constraint. If too large, the other devices may injure the ocular punctum tissue upon insertion. If too small, the retention may be ineffective.

There are several factors working on an implanted device to encourage loss both internally (migration into the canalicular lumen wherein the device is "lost" and the drug eluting element can no longer come in contact with the tear fluid) and externally (where the device is released or expelled from the ocular punctum). These factors include rubbing of the eyes; nose blowing or sneezing; and blinking, squinting or other manipulation of musculature around the eye. The mechanical manipulation of the eyelid and tissues surrounding the eye from rubbing with the hand or finger can impose significant forces on a punctal implant device to cause to be displaced from its nominal position. This displacement can then result in the migration into or being expelled from the ocular punctum. Significant pressure and amounts of air flow can build up in the canalicular lumen during nose blowing or sneezing events. As a punctal implant device seals the ocular punctum, these effects induce forces on the devices to displace it externally and encourage it to be expelled. These natural movements of blinking and squinting induce pressure and force on the ocular punctum and subsequently the a punctal implant device. These forces can cause the device to displace and either migrate internally into the canalicular lumen or externally and be expelled.

The use of SMP materials in ophthalmological devices as disclosed herein provides the ability to deploy much larger and more complex features in order to enhance plug retention in-situ. Further, the nature of these features can be designed to provide for differential action to allow for ease of insertion, removal, and enhanced patient comfort during deployment and wear. The mechanical properties of SMP materials can be tailored to achieve stiffness or softness for each aspect of insertion or wear.

In general, the ophthalmological punctal plug device disclosed herein and described in more detail below includes a body with a resilient anchor wherein both have an extended or expanded memory shape (deployed state) that can be maintained in a temporary compacted or constrained shape (non-deployed state) for introduction into the ocular punctum. Upon insertion (introduction into the ocular punctum), the body temperature stimulates the shape change to achieve two primary beneficial effects related to reliable retention. First, energy that is stored within the constrained device (in the non-deployed state) is released in the transition from non-deployed state to deployed state to thereby apply retention forces to the ocular punctum and cannicular lumen. The punctal plug device maintains some active force on the anatomical structure, yet is benign so as not to cause discomfort or injury. Second, features on the body and anchor are deployed or expand from the shape change resulting in device sizes below and above the ocular punctum that are larger than the ocular punctum ostium diameter, thereby fixing the plug reliably within the ocular punctum.

Also, the implantable ophthalmological device is generally small in order to be received in the small punctal opening. The ocular punctum size and anatomy varies between patients but generally is within 1-2 mm in diameter. The canalicular lumen extends about 2.5 mm below the ocular punctum and then curves sharply to turn toward the nasal cavity in the head. The device may reside in this lumen without causing undue irritation and discomfort and/or the generation of significant inflammation, granuloma, or inducing infection.

Figure 2:
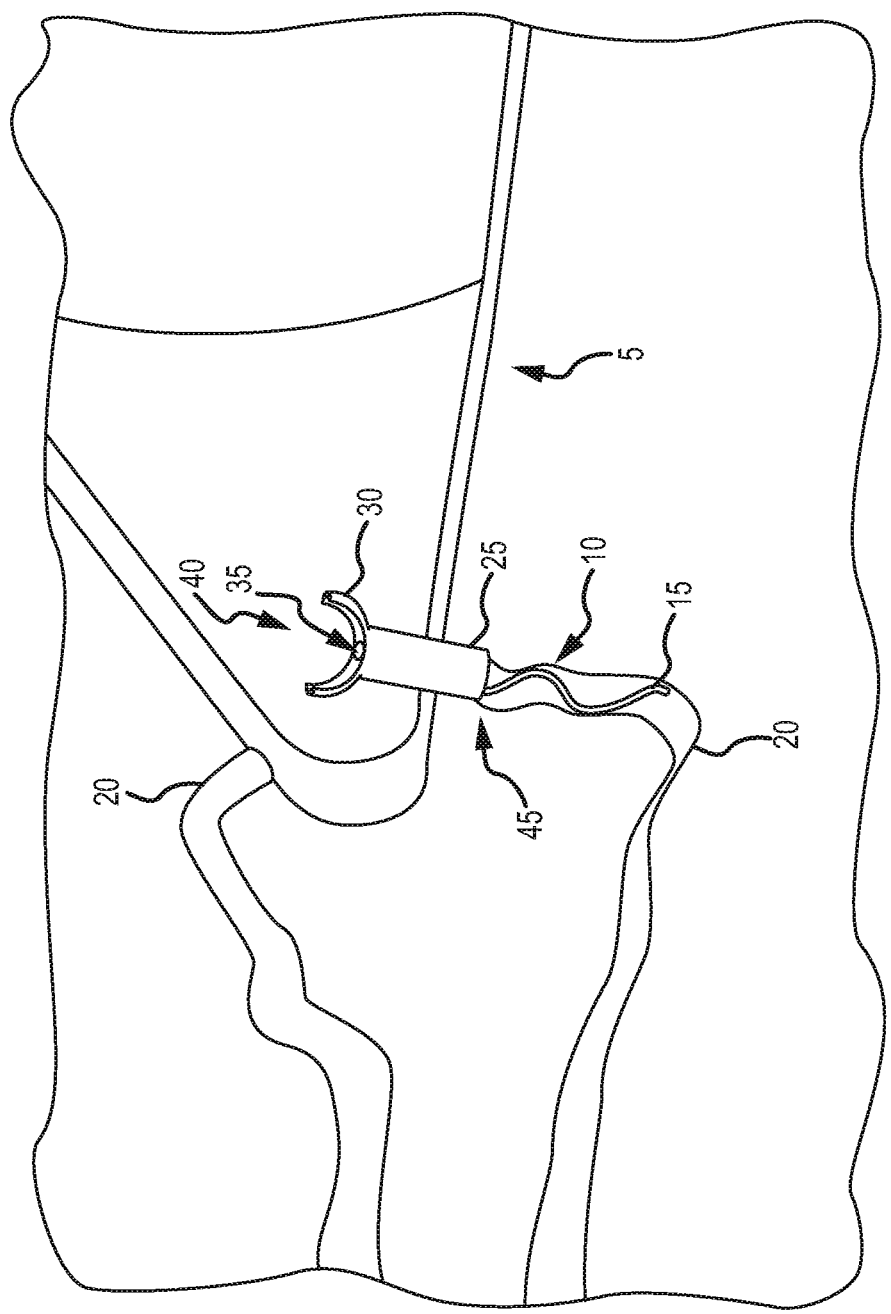
FIG. 2 is a partially transparent, schematic view of the device as shown in FIG. 1 with the anchor shown in a partially deployed state.
Figure 3:
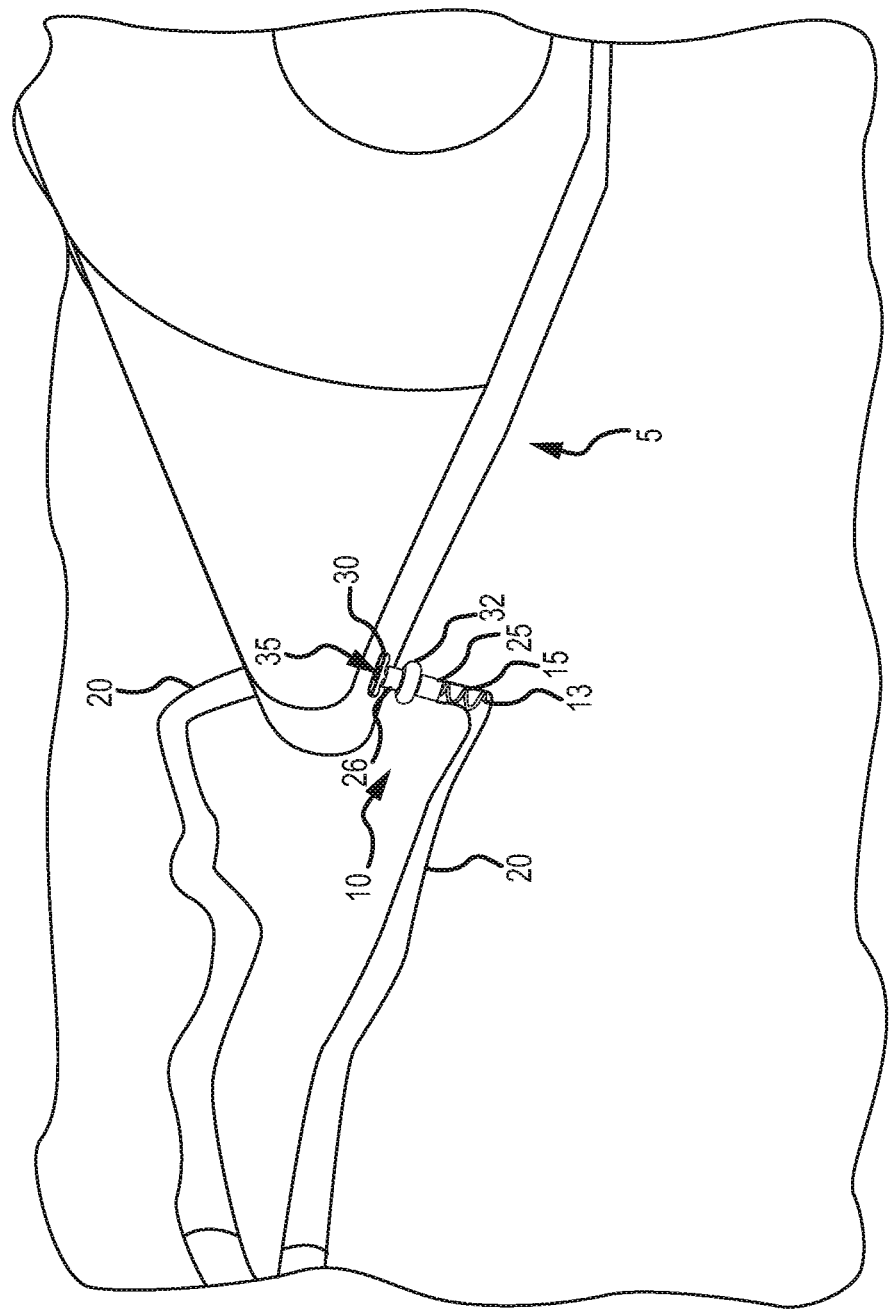
FIG. 3 is a partially transparent, schematic view of the device as shown in FIG. 2, with the device shown in a deployed state.
Figure 4:
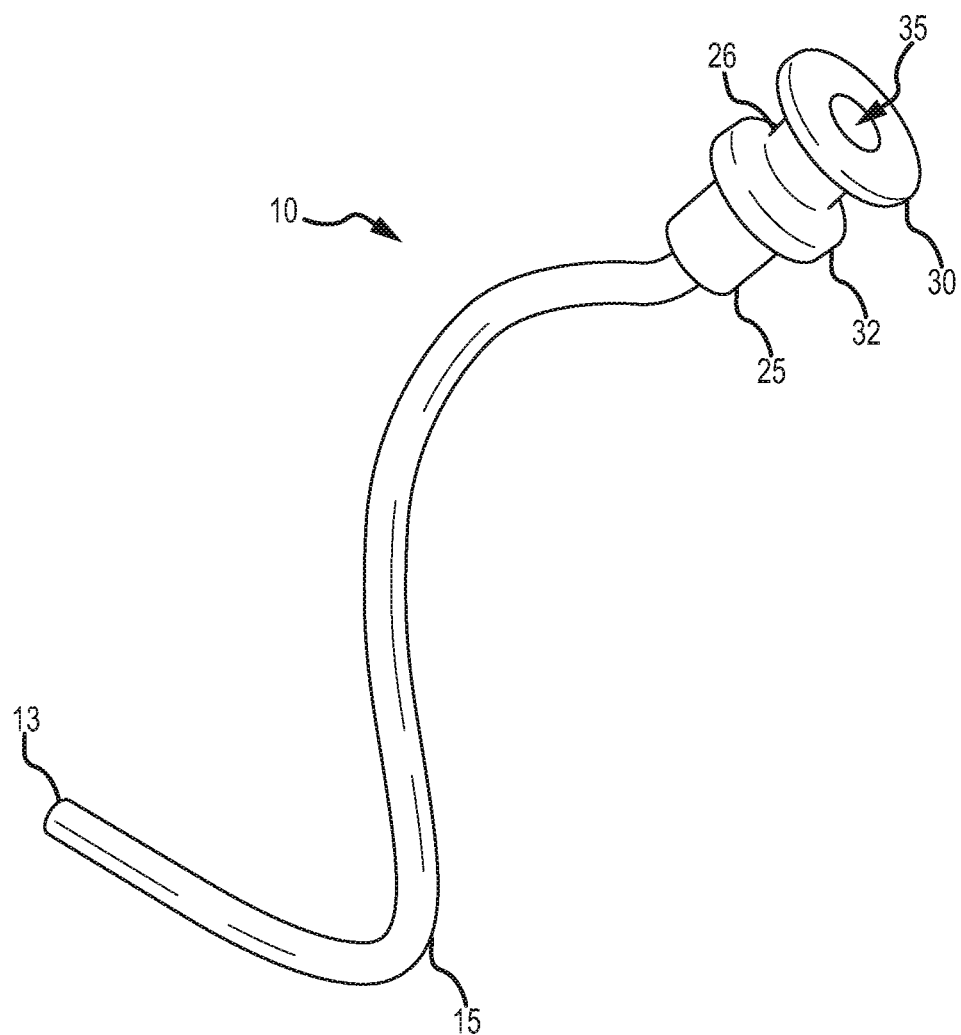
FIG. 4 is an isometric view of the device of FIG. 1 in a deployed state in an isolated environment.

For a general description of the implantable ophthalmological device, reference is now made to FIGS. 1-6B. FIG. 1 is an exemplary implementation of a partially transparent, schematic view of an implantable ophthalmological device 10 including an anchor 15, wherein the device is shown in a non-deployed state as it is implanted in a human eye 5 and, more specifically, a ocular punctum 20 of the human eye 5. FIG. 2 is a further view of the device 10 as shown in FIG. 1, except the anchor 15 is shown in a partially deployed state. FIG. 3 is another view of the device 10 as shown in FIG. 2, except the device 10 is shown in a deployed state. FIGS. 4-6B depict various embodiments of implantable ophthalmological devices that may be deployed in a patient's ocular punctum in the manner depicted in FIGS. 1-3.

As can be understood from FIGS. 1-6B, the device 10 may include an elongated body 25, an anchor 15, a flange 30, and an occlusive feature 32. The device 10 may be made of a shape memory polymer (SMP). SMPs demonstrate the phenomena of shape memory based on fabricating a segregated linear block co-polymer, typically of a cross-linked hard segment and a soft segment. In one implementation, the SMP is a chemically cross-linked, and therefore homogeneous, polymer consisting of a mono-functional, backbone monomer and a di-functional, cross-linker monomer. When combined properly, these ingredients polymerize randomly, producing a homogeneous matrix. The shape memory polymer may be generally characterized by defining phases that result from glass transition temperatures ($T_g$) in the hard and soft segments. Mechanical properties of the phases, stored shape or non-deployed state (e.g., below the $T_g$) and the deployed shape (e.g., above the $T_g$), as well as setting the $T_g$, can be tailored by adjusting the formulation through different weight percentages of the monomers and cross linker. The device 10 may be made of a shape memory polymer as described in related International Application No. PCT/US2007/065691, entitled "Shape memory polymer medical devices," and filed 30 Mar. 2007, which is incorporated by reference herein in its entirety. In some embodiments, the device may be made of a shape memory metal alloy.

The SMP or shape memory metal alloy provides the ability for significant shape change and shape fixity of body features that may improve insertion and retention. The SMP materials may also provide for a conformed/constrained storage shape (i.e., the non-deployed state) that minimizes the profile and eases entry past the ocular punctum into the cannicular lumen without stressing the ocular punctum. This property may be referred to as "shape fixity" and enables unique configurations/shapes for insertion, in-situ use, and removal. It provides the ability for significant shape change and shape fixity of body, occlusive features, and anchor to allow a reduced, smoother configuration. When used for insertion into the small ocular punctum and upon exposure to body temperature, the SMP ophthalmological device deploys to a defined shape with features that enhance retention capabilities. These two definitive shapes (i.e., the non-deployed shape and the deployed shape) may be advantageous over other elastomeric or flexible materials undergoing compression within an elastic range of such elastomeric material.

As shown in FIGS. 1-6B, the elongated body 25 includes a distal end 45 and a proximal end 40. In some embodiments, the elongated body 25 defines a lumen or cavity 35 extending longitudinally therein. The lumen 35 may be configured to receive a pharmaceutical preparation 55, such as a drug capsule, a lyophilized powder/tablet, or a matrix of drug/polymer that dissolves. In use, the pharmaceutical preparation may dissolve and/or elute a therapeutic agent (drug) into the tear fluid. In some embodiments, the pharmaceutical preparation includes retention features on its surface and the lumen 35 may be configured to receive such features. These features could degrade or dissolve over time, thereby easing removal and replacement of the capsule. The body 25 may include slots, apertures, or other forms of fenestration to aid in the release of the pharmaceutical preparation.

As indicated in FIGS. 1-6B, an anchor 15 may be operably attached to the distal end 45 of the elongated body 25. Given the inelastic strain of SMP materials, an anchor may be formed with numerous features in its memory shape. The anchor may be conformed to a benign or atraumatic insertion shape and retain this temporary, non-deployed shape while being maintained below its $T_g$ and constrained within an insertion tube or cannula. Once the device 10 is introduced through the ocular punctum and expelled from the insertion tube, the body's local temperature affects the SMP and the anchor 15 and elongated body 25 each return to their memory shape or deployed state. Features of the anchor 15 engage with soft tissue below the punctal ostium thereby providing a significant retention interface. The anchor 15 may be a spiral or helical coil-shape, a ring or shape, or other shape with one or more branches, or made of a round or non-round cross section that aids in the retention of the device in the ocular punctum 20. In some embodiments, a distal end 13 of the anchor 15 might include, for example, and not by way of limitation, a balloon, a sponge or foam part, or a barb with a split down the middle.

Figure 5A:
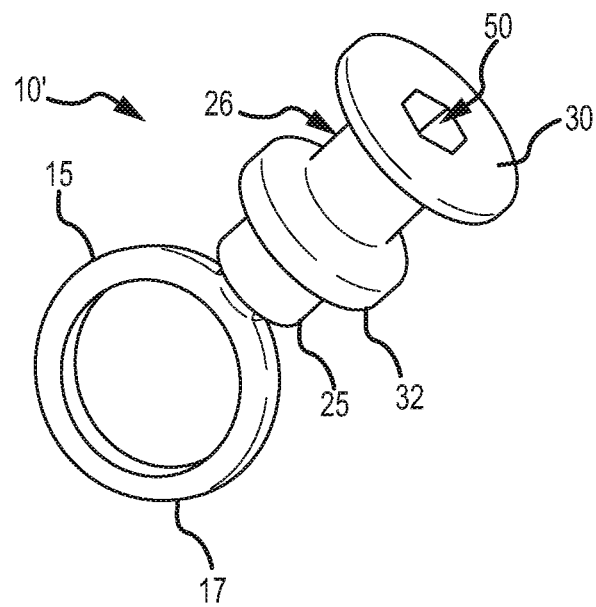
FIG. 5A is an isometric view of another embodiment of an implantable ophthalmological device including an anchor wherein the device is shown in a deployed state.
Figure 5B:
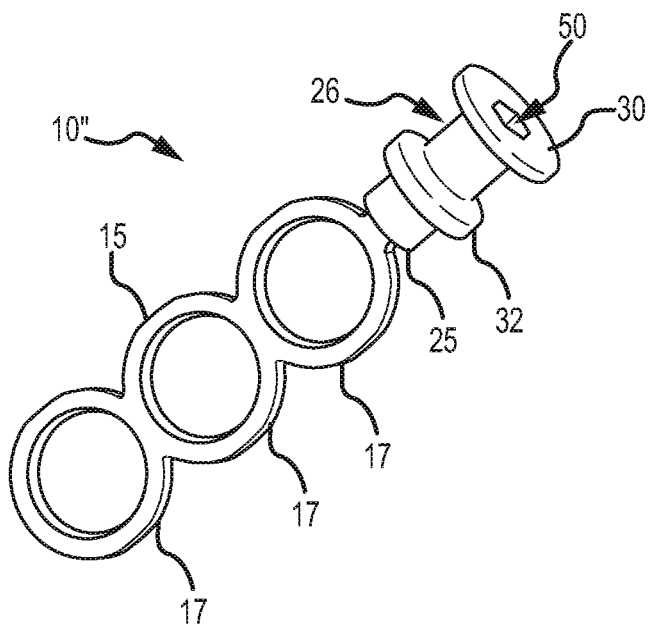
FIG. 5B is an isometric view of a further embodiment of an implantable ophthalmological device including an anchor wherein the device is shown in a deployed state.
Figure 6A:
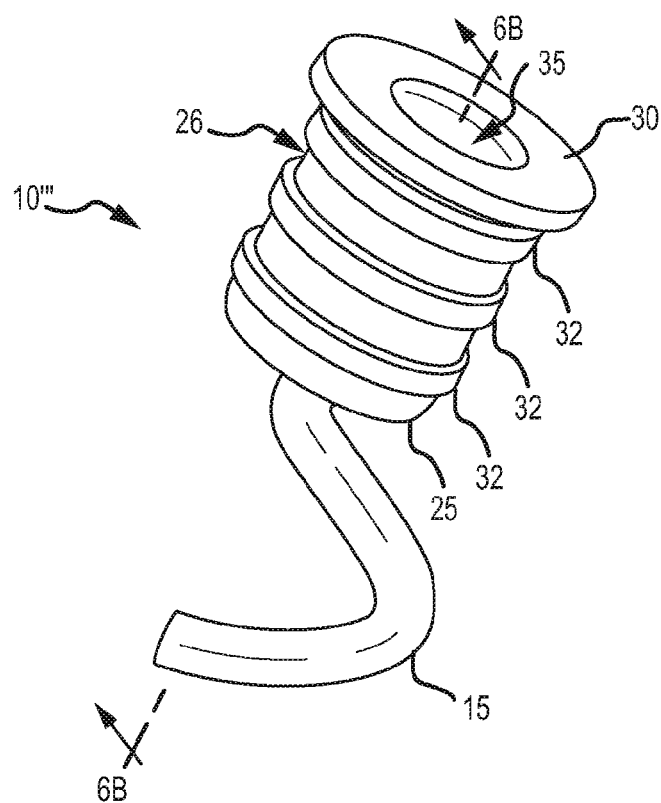
FIG. 6A is an isometric view of still another embodiment of an implantable ophthalmological device including an anchor wherein the device is shown in a deployed state.
Figure 6B:
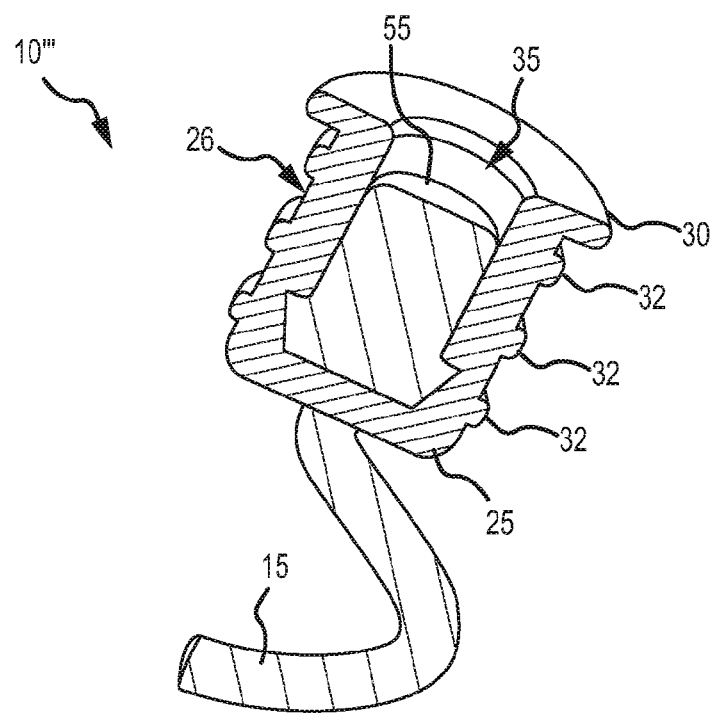
FIG. 6B is a cross-section view of the device of FIG. 6A along section line 6B-6B shown in FIG. 6A.

As shown in FIGS. 5A-5B, in exemplary embodiments of devices 10' and 10", the anchor 15 may have a circular form that represents a specialized shape of one or more circular rings 17, wherein the anchor 15 can change its function and interaction with different movement. The circular anchor 17 may be constrained and deployed in a narrow, benign configuration, and later expand in response to the body temperature. In a deployed state, the rings 17 are larger than the ocular punctum 20 and engage in a non-irritating manner with the cannicular lumen surface. The circular anchor 17 may provide good retention in opposition to certain forces operating axially on the device (e.g., internal forces such as sneezing or external forces such as rubbing).

In some embodiments, the body 25 and/or the flange 30 may be configured to receive a key member in a keyway 50 as shown in FIGS. 5A and 5B. When the devices 10', 10" are rotated or twisted by the inserted key member, the circular anchors 17 may be configured to fold or collapse into a smaller profile structure enabling the removal of the devices 10', 10" without significant stress to the ocular punctum.

The anchor features 15 may be configured to be large, or very aggressive against axial displacement and forces, but then can be folded or collapsed when rotational/twisting forces are applied to reduce their profile to a small shape or size that can be easily removed. Such a shape may be considered an atraumatic removal shape. In the non-deployed state, the anchor may be smooth and relatively straight. The diameter of the anchor may be small to pass through the punctal ostium (0.5 mm max) without inducing damage to the ostium.

As can be understood from FIGS. 3-6B, a radially expanding occlusive feature 32 may be disposed about an outer circumference 26 of the body 25. The feature may be incorporated in/onto the body 25 and may be formed to provide seals against the ocular punctum or cannicular lumen in its memory shape or deployed state. In some embodiments (e.g. FIGS. 3-5B), there may be one feature 32. In other embodiments (e.g. FIGS. 6A-6B), there may be more than one feature 32. The occlusive feature 32 is not so large in diameter as to tear the punctal ostium during removal because it is not the primary means for retention. As shown in the figures, the occlusive feature 32 may be circular or disc-shaped, but it may take the form of various other geometric or irregular shapes in order to best occlude a particular lumen in which it is seated.

In use, the occlusive features 32 are conformed to a temporary benign insertion shape and constrained inside of an insertion lumen. Once introduced into the ocular punctum, a change in temperature past $T_g$ cause these occlusive features 32 to deploy and return to the memory shape. With an increase in diameter, these occlusive features 32 engender a seal against the cannicular lumen. The body 25 maintains a radially expanding sealing or occlusive feature(s) 32 that expand with temperature stimulus to provide a compliant seal against the ocular punctum.

As indicated in FIGS. 1-6B, the device 10, 10', 10" may also include a flange 30. The flange helps prevent the device from being completely drawn into the cannicular lumen. The flange 30 may be round or may be oval shape to allow orientation to minimize any irritation resulting from possible contact with the eye.

The features of the anchor 15, body 25, and flange 30 provide reliable retention of the plug 10, 10', 10". For example, the resilience or compliance of the anchor 15 isolates the plug motion from the distal portion 13 of the anchor 15. The anchor 15 may act like a spring, isolating motion of one end from the other. This configuration provides significant value in retention as the plug body 25 may be momentarily displaced or shifted from external influences (e.g., sneezing or rubbing). Yet, when this external influence is removed, the anchor 15 pulls the body 25 back into proper position.

However, the anchor 15 may be designed to not present a significant mass at the distal end within the cannicular lumen and as such, will not be affected by these external influences. The distal end of the anchor is relatively stable. Also, the radially expanding occlusive feature 32 of the body 25 provides resistance from movement by engaging with the punctal ostium. Further, the flange 30, being larger in diameter than the punctal ostium, prevents migration of the plug 10, 10', 10" into the canniular lumen. Thus, the device 10, 10', 10" may be easily/simply inserted, deploy significant features for reliable retention after insertion, and maintain a flexibility and softness to ensure patient comfort both internally and externally. Specifically, the SMP device 10, 10', 10" can enter the narrow ocular punctum opening and expand to deploy certain features to provide good mechanical capture and retention.

The ocular punctum and the cannicular lumen are anatomical structures and, as such, present dimensional variability patient to patient, but these dimensions are within known ranges. A plug 10, 10', 10" placed in the ocular punctum intending to provide reliable retention may account for the anatomical variability, including the diameter and thickness of the ocular punctum (and/or its ostium), the diameter of the cannicular lumen, and the length of the lumen before it turns toward the sinus, among others. This variability may present a challenge to other devices molded of flexible or elastomeric polymers that can only accommodate limited elastic strain (e.g., compression or stretch). Conversely, SMP materials are capable of very high strain rates above traditional polymers, allowing greater amounts of mechanical and dimensional shape change than can be achieved with traditional polymers and elastomers. This capability allows an SMP device to accommodate greater anatomical variability than a similar sized device of traditional polymer or elastomer.

In use, the anchor 15, body 25 (including the occlusive feature 32), and flange 30 are in a compacted form or non-deployed state within an instrument used to insert the plug 10, 10', 10". A delivery instrument may provide a tube (e.g., a cannula), that holds the device 10, 10', 10" with these three features in a non-deployed state. The tube is aligned and pressed up against the punctal ostium. As directed by the user's fingers, the instrument may provide a plunger that through a simple action of pushing a pin within the tube, the device 10, 10', 10" slides out of the tube into the ocular punctum wherein the resilient anchor 15 enters the cannicular lumen first, followed by the body 25. The pin position may restricted from introducing the device 10, 10', 10" too far into the ocular punctum. The body 25 is positioned at the ostium. The occlusion features 32 of both the anchor 15 and the body 25 respond to the temperature and deploy to their larger shape holding the device 10, 10', 10" in place. The delivery instrument may then be withdrawn releasing the flange 30 of the plug 10, 10', 10" which is maintained external to the ocular punctum.

Figure 7A:
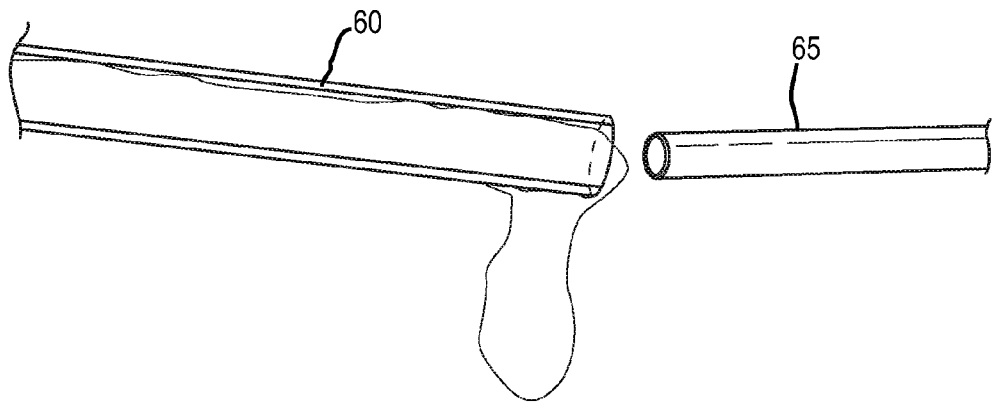
FIGS. 7A-7G are a series of schematic views depicting the delivery of an implementation of an implantable ophthalmological device into a lumen and transitioning from a non-deployed state into a deployed state to arrest the flow of fluid in the lumen.
Figure 7B:
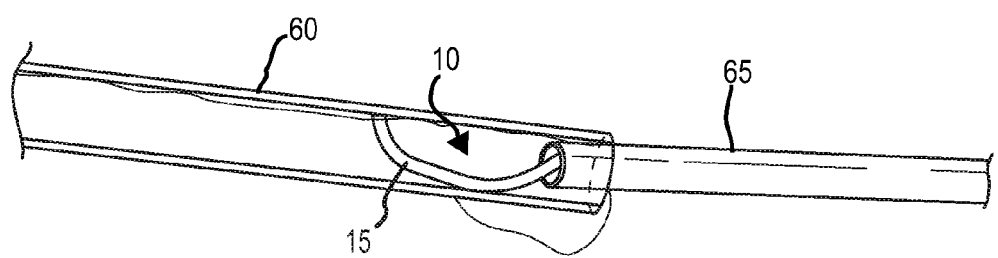
Figure 7C:
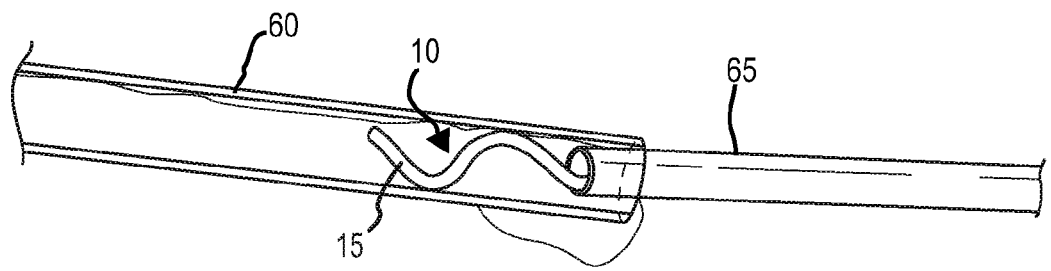
Figure 7D:
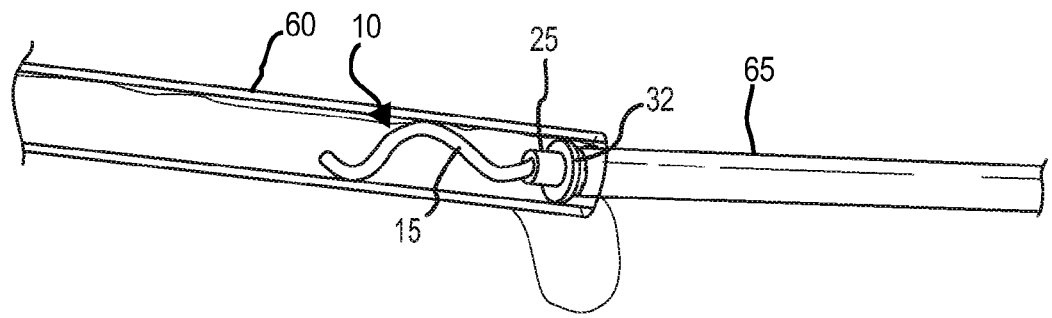
Figure 7E:
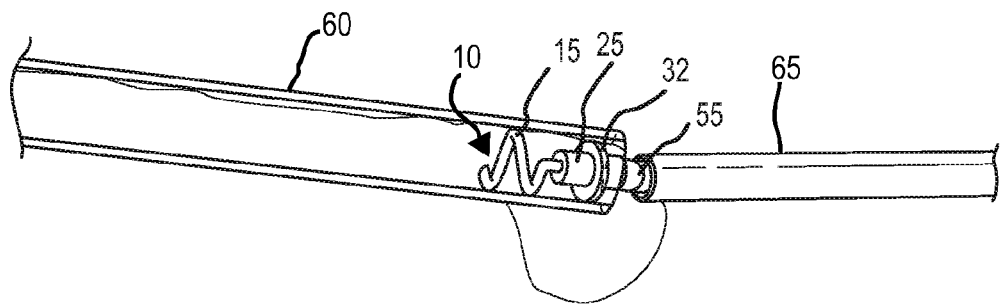
Figure 7F:
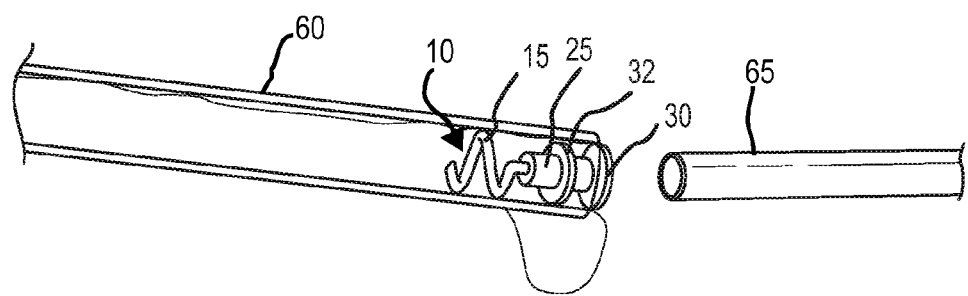
Figure 7G:
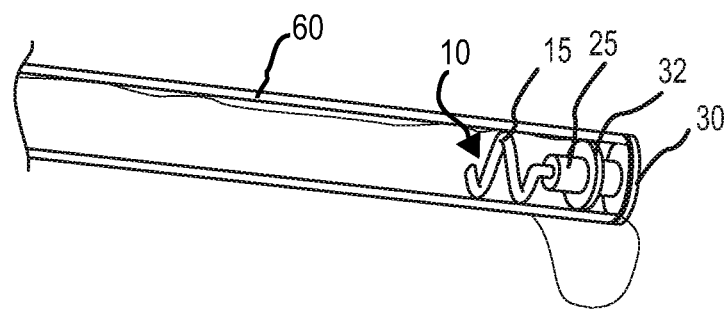

FIGS. 7A-7G are a series of schematic diagrams depicting an implementation of an implantable ophthalmological device transitioning from a non-deployed state into a deployed state. The left-hand sides of the diagrams depict a cannula 60 with a warm water flow initially exiting a distal end of the cannula as in FIG. 7A. A deployment tube 65 is shown from the right-hand side to insert a SMP plug similar to the embodiment of FIGS. 1-4 into the cannula as shown in FIG. 7B. As the SMP plug 10 is introduced to the warm water, the $T_g$ for the SMP material is reached and the SMP plug transforms from a non-deployed state to a deployed state within the cannula 60. In FIG. 7C, the anchor 15 begins to curl as the remaining portions of the device 10 continue to be delivered into the cannula 60. FIG. 7D shows the occlusive feature 32 beginning to expand about the plug body 25 within the cannula 60 upon exposure to the warm water. In FIG. 7E the plug device 10 has been completely delivered from the deployment tube 65 by a deployment catheter 55. FIG. 7F shows the occlusive feature 32 and the flange 30 increasing in diameter until the occlusive feature 32 fits snugly against the inner wall of the cannula 60 and the flange 30 is larger in diameter than the inner diameter of the cannula 60. As the occlusive feature 32 and the flange 30 expand, the water flow though the cannula 60 decreases until it is fully stopped and the plug device 10 is restricted from migration into and out of the lumen of the cannula 60 as shown in FIG. 7G.

Although the device provides several retention features, it may be desirable to intentionally remove the device without damaging the ostium of the ocular punctum, such as when the pharmaceutical preparation must be replaced or otherwise altered (e.g., the eluting matrix is depleted and needs to be replaced). While the soft tissue of the ostium can stretch slightly, large forces or displacements can result in injury or tearing of the ostium. If the ostium is injured or torn from removal, such that it is expanded in size, the ability to reliably retain a replacement plug may be compromised as the diameter and interface has changed. With some therapies prescribing multiple plug replacements during the course of a year, the potential for continual degradation of plug retention is significant, causing patents with a longer history of using drug delivery punctal plugs to suffer lower retention rates undermining the efficacy of the therapy. However, with the presently disclosed device, the occlusive feature is not so large in diameter as to tear the punctal ostium during removal because it is not the primary means for retention.

Also, the resilient anchor may respond in a different manner to different external influences through the material properties and the cross-section of the anchor. The deployed anchor is expanded and provides good retention and stability when the plug is momentarily displaced along the central axis of the ocular punctum, e.g., from sneezing or rubbing. However, when the plug is intentionally rotated through a keyed opening in the flange, via the key member, the anchor may collapse into an organized shape that is small and prevents the device from causing injury to the ostium. Upon rotation, the anchor features may group and align such that the anchor mimics a thread shape that may prevent ostium injury and help in the removal of the device upon continued rotation of the device by the key member.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A shape memory polymer plug configured for use in occluding an ocular punctum comprising in a pre-deployed state, a constrained, smooth, and relatively straight but flexible body formed entirely of the shape memory polymer; and in a deployed state,
an elongate body having a proximal end and a distal end;
an anchor protruding directly and extending distally away from the distal end surface of the elongate body, wherein at least a portion of the anchor forms a structure that is wider than a diameter of the ocular punctum; and
a flange extending from the proximal end of the elongate body in a plane generally perpendicular to a longitudinal orientation of the elongate body; wherein
the elongate body, the anchor, and the flange are formed as a monolithic structure entirely of the shape memory polymer which transitions from the pre-deployed state to the deployed state upon exposure to an external stimulus; and
the anchor is configured to collapse upon rotation of the elongate body allow for substantially atraumatic removal of the device from the ocular punctum.

2. The device of claim 1, wherein the elongate body further defines a lumen extending longitudinally therein.

3. The device of claim 2, wherein the lumen of the elongate body is configured to receive a pharmaceutical preparation.

4. The device of claim 3 further comprising a pharmaceutical preparation contained within the lumen.

5. The device of claim 3, wherein the elongate body is fenestrated to allow a pharmaceutical preparation to elute from the lumen at multiple locations.

6. The device of claim 2, wherein
the lumen of the elongate body is configured to receive a key; and
the anchor is configured to collapse upon rotation of the elongate body by a key received in the lumen to allow for substantially atraumatic removal of the device from the ocular punctum.

7. The device of claim 2, wherein
the flange is configured to receive a key; and
the anchor is configured to collapse upon rotation of the elongate body by a key received in the flange to allow for substantially atraumatic removal of the device from the ocular punctum.

8. The device of claim 1, wherein the flange is formed as an annular ring.

9. The device of claim 1, wherein the radially occlusive feature comprises a plurality of annular rings separated longitudinally along the outer surface of the elongate body.

10. The device of claim 1, wherein the anchor is formed as a spiral coil.

11. The device of claim 1, wherein the anchor is formed as a ring connected tangentially to the elongate body.

12. The device of claim 1, wherein the anchor is formed as a plurality of rings with a first ring of the plurality of rings connected tangentially to the elongate body and each successive ring of the plurality of rings connected tangentially to an immediately prior one of the plurality of rings.

13. The device of claim 1, wherein the anchor is formed as a split barb.

14. The device of claim 1, wherein the anchor is formed with a plurality of branches.

15. The device of claim 1 further comprising, in the deployed state, a radially extending occlusive feature disposed on an outer surface of the elongate body.

16. The device of claim 15, wherein the radially extending occlusive feature comprises an annular ring.

* * * * *